US00PP14051P29

(12) United States Plant Patent
Post

(10) Patent No.: US PP14,051 P2
(45) Date of Patent: Aug. 5, 2003

(54) CHRYSANTHEMUM PLANT NAMED 'CAYENNE'

(75) Inventor: Arie Gerard Post, PT 's-Gravenzande (NL)

(73) Assignee: Deliflor Royalty B.V., Maasdijk (NL)

( * ) Notice: Subject to any disclaimer, the term of this patent is extended or adjusted under 35 U.S.C. 154(b) by 0 days.

(21) Appl. No.: 10/094,315

(22) Filed: Mar. 8, 2002

(51) Int. Cl.[7] ..... A01H 5/00
(52) U.S. Cl. ..... Plt./298
(58) Field of Search ..... Plt./286, 298

*Primary Examiner*—Howard J. Locker
(74) *Attorney, Agent, or Firm*—C. A. Whealy

(57) ABSTRACT

A distinct cultivar of Chrysanthemum plant named 'Cayenne', characterized by its daisy inflorescence form with dark red-colored ray florets; dark green foliage; strong flowering stems; freely flowering habit; short response time; and excellent postproduction longevity.

1 Drawing Sheet

BOTANICAL CLASSIFICATION/CULTIVAR DESIGNATION

*Chrysanthemum×morifolium* cultivar Cayenne.

BACKGROUND OF THE INVENTION

The present invention relates to a new and distinct cultivar of Chrysanthemum plant, botanically known as *Chrysanthemum×morifolium* and referred to by the name 'Cayenne'.

The new Chrysanthemum originated from a cross-pollination made by the Inventor in 's-Gravenzande, The Netherlands, of a proprietary selection of Chrysanthemum identified as code number DB 8877, not patented, as the female, or seed, parent with a proprietary selection of Chrysanthemum identified as code number DB 20646, not patented, as the male, or pollen, parent. The new Chrysanthemum was discovered and selected by the Inventor within the progeny of the stated cross in a controlled environment in 's-Gravenzande, The Netherlands, in January, 2001. The selection of this plant was based on its inflorescence form, color and good substance.

Asexual reproduction of the new Chrysanthemum by terminal cuttings harvested in 's-Gravenzande, The Netherlands since January, 2001, has shown that the unique features of this new Chrysanthemum are stable and reproduced true to type in successive generations.

BRIEF SUMMARY OF THE INVENTION

The cultivar Cayenne has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Cayenne'. These characteristics in combination distinguish 'Cayenne' as a new and distinct cultivar:

1. Daisy inflorescence form with dark red-colored ray florets; typically grown as a spray type.

2. Dark green foliage.

3. Strong flowering stems.

4. Freely flowering habit.

5. Short response time.

6. Excellent postproduction longevity.

Plants of the new Chrysanthemum can be compared to plants of the female parent, the selection DB 8877. In side-by-side comparisons conducted by the Inventor in 's-Gravenzande, The Netherlands, plants of the new Chrysanthemum differed from plants of the selection DB 8877 in the following characteristics:

1. Plants of the new Chrysanthemum were more uniform and more vigorous than plants of the selection DB 8877.

2. Plants of the new Chrysanthemum had paler green-colored leaves than plants of the selection DB 8877.

3. Ray florets of plants of the selection DB 8877 were more rounded than ray florets of plants of the new Chrysanthemum.

Plants of the new Chrysanthemum can be compared to plants of the male parent, the selection DB 20646. In side-by-side comparisons conducted by the Inventor in 's-Gravenzande, The Netherlands, plants of the new Chrysanthemum and the selection DB 20646 differed in the following characteristics:

1. Plants of the new Chrysanthemum had stronger stems than plants of the selection DB 20646.

2. Plants of the new Chrysanthemum had shorter internodes than plants of the selection DB 20646.

3. Disc florets of plants of the new Chrysanthemum developed slower than disc florets of plants of the selection DB 20646.

Plants of the new Chrysanthemum can also be compared to plants of the cultivar Tigerrag, not patented. In side-by-side comparisons conducted by the Inventor in 's-Gravenzande, The Netherlands, plants of the new Chrysanthemum and the cultivar Tigerrag differed in the following characteristics:

1. Plants of the new Chrysanthemum had more inflorescences per flowering stem than plants of the cultivar Tigerrag.

2. Inflorescences of plants of the new Chrysanthemum were more rounded than inflorescences of plants of the cultivar Tigerrag.

3. Ray florets of plants of the new Chrysanthemum had more rounded apices than ray florets of the cultivar Tigerrag.

4. Ray florets of plants of the new Chrysanthemum were darker red in color than ray florets of plants of the cultivar Tigerrag.

5. Plants of the new Chrysanthemum flowered about six days earlier than plants of the cultivar Tigerrag.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Chrysanthemum.

The photograph at the top of the sheet comprises a side perspective view of a typical flowering stem of 'Cayenne'.

The photograph at the bottom of the sheet comprises a close-up view of a typical leaf and a typical inflorescence of 'Cayenne'.

DETAILED BOTANICAL DESCRIPTION

In the following description, color references are made to The Royal Horticultural Society Colour Chart except where general terms of ordinary dictionary significance are used. The aforementioned photographs, following observations and measurements describe plants grown in ground beds in 's-Gravenzande, The Netherlands, under commercial practice in a glass-covered greenhouse. Plants were initially given short nyctoperiods followed by long nyctoperiods to induce flower initiation and development. Average day and night temperatures were 18 and 19° C., respectively. Plants were grown as single-stem spray types and were about 11 weeks from planting when the photographs and description were taken.

Botanical classification: *Chrysanthemum×morifolium* cultivar Cayenne.

Commercial classification: Cut Chrysanthemum with daisy inflorescence form; typically grown as a spray-type.

Parentage:

*Female or seed parent.*—Proprietary selection of *Chrysanthemum×morifolium* identified as code number DB 8877, not patented.

*Male or pollen parent.*—Proprietary selection of *Chrysanthemum×morifolium* identified as code number DB 20646, not patented.

Propagation:

*Type.*—Terminal tip cuttings.

*Time to initiate roots, summer.*—About 5 days at 20° C.

*Time to initiate roots, winter.*—About 6 days at 20° C.

*Root description.*—Fine, fibrous and well-branched.

Plant description:

*Appearance.*—Herbaceous cut Chrysanthemum with daisy inflorescence form; typically grown as a spray type. Upright with strong stems.

*Growth rate.*—Moderate; moderately vigorous.

*Crop time.*—For cut flowers, about 11 weeks are required to produce flowering stems.

*Flowering stem description.*—Length: About 80 cm. Diameter, at base: About 6 mm. Strength: Strong. Aspect: Upright. Branching habit: Plants are typically grown as single stems. Color: 144A.

*Foliage description.*—Arrangement: Alternate. Length: About 11.5 cm. Width: About 7 cm. Apex: Mucronate. Base: Obtuse to truncate. Margin: Palmately lobed. Texture, upper and lower surfaces: Rough; pubescent. Petiole length: About 2.5 cm. Color: Young foliage, upper surface: 137A. Young foliage, lower surface: 137C. Fully expanded foliage, upper surface: Darker than 137A. Fully expanded foliage, lower surface: Darker than 147B. Venation: Upper surface: 146A. Lower surface: 146B. Petiole: 146B.

Inflorescence description:

*Appearance.*—Daisy inflorescence form. Inflorescences borne on terminals, arising from leaf axils. Ray and disc florets arranged acropetally on the receptacle.

*Flowering response.*—Under natural conditions, plant typically flowers in November in the Northern Hemisphere. At other times of the year, inflorescence initiation and development can be induced under long nyctoperiod conditions (at least 13.5 hours of darkness). Early flowering; plants exposed to short nyctoperiods conditions after planting followed by photoinductive long nyctoperiod conditions flower about 7.5 weeks later.

*Postproduction longevity.*—Inflorescences will maintain good substance and form for about 5 weeks on the plant and for about 3 weeks after harvesting cut flowering stems.

*Quantity of inflorescences per flowering stem.*—About 15.

*Inflorescence size.*—Diameter: About 5 cm. Depth (height): About 2 cm. Diameter of disc: About 1.3 cm.

*Inflorescence buds.*—Length: About 6 mm. Diameter: About 8 mm. Shape: Oblate. Color: 148B.

*Ray florets.*—Length: About 2.5 cm. Width: About 1 cm. Shape: Elongated oblong. Apex: Rounded. Base: Acute to attenuate. Margin: Entire. Texture: Smooth, glabrous. Number of ray florets per inflorescence: About 25. Color: When opening, upper surface: 59A. When opening, lower surface: 185A. Fully opened, upper surface: Close to 59A. Fully opened, lower surface: 184B.

*Disc florets.*—Shape: Oblong, tubular. Length: About 4 mm. Width: About 1 mm. Number of disc florets per inflorescence: About 220. Color: Immature: 144C. Mature: 144B.

*Peduncles.*—Length, terminal peduncle: About 4 cm. Length, fourth peduncle: About 5 cm. Diameter: About 2 mm. Angle: About 60 to 80° to main stem. Texture: Pubescent. Color: 138A.

*Reproductive organs.*—Androecium: Present on disc florets only. Anther color: 12A. Amount of pollen: Moderate. Pollen: 12A. Gynoecium: Present on both ray and disc florets.

*Seed.*—Seed production has not been observed.

Disease/pest resistance: Resistance to known Chrysanthemum pathogens and pests has not been observed on plants of the new Chrysanthemum.

It is claimed:

1. A new and distinct cultivar of Chrysanthemum plant named 'Cayenne', as illustrated and described.

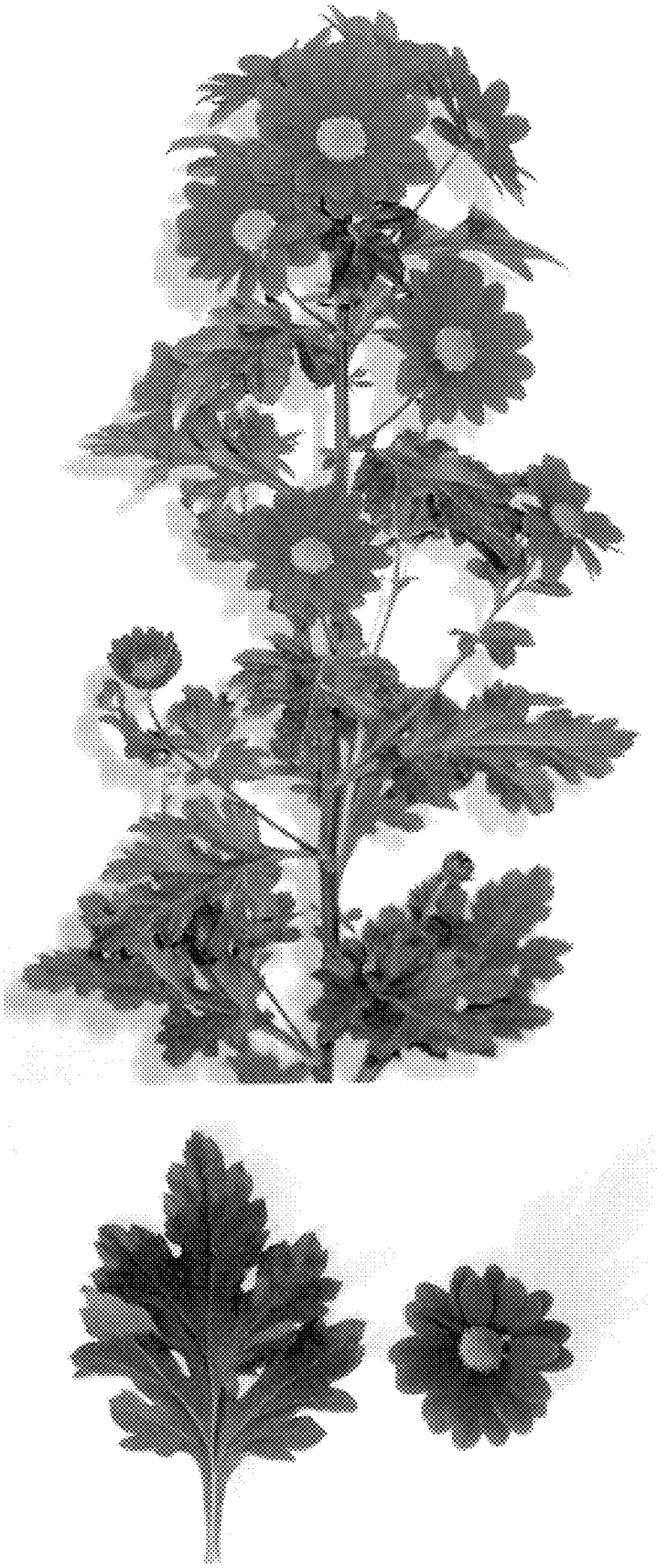

* * * * *